US00PP32858P2

(12) United States Plant Patent

Klemm et al.

(10) Patent No.: US PP32,858 P2
(45) Date of Patent: Mar. 2, 2021

(54) *DIANTHUS* PLANT NAMED 'KLEDP19263'

(50) Latin Name: *Dianthus caryophyllus*
Varietal Denomination: KLEDP19263

(71) Applicant: Klemm+Sohn GmbH & Co. KG, Stuttgart (DE)

(72) Inventors: Nils Klemm, Stuttgart (DE); Lena Thiede, Bempflingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/873,273

(22) Filed: Mar. 10, 2020

Related U.S. Application Data

(60) Provisional application No. 62/973,971, filed on Nov. 4, 2019.

(51) Int. Cl.
*A01H 5/02* (2018.01)
*A01H 6/30* (2018.01)

(52) U.S. Cl.
USPC ..... Plt./273
CPC ..... *A01H 6/305* (2018.05)

(58) Field of Classification Search
USPC ..... Plt./273
CPC ..... A01H 6/305; A01H 5/02
See application file for complete search history.

*Primary Examiner* — Keith O. Robinson
(74) *Attorney, Agent, or Firm* — Weatherly IP Solutions, LLC; Barbara Campbell

(57) ABSTRACT

A new *Dianthus* plant designated 'KLEDP19263' particularly distinguished by pink double flowers with red eyes, composed in round, small sprays and an upright habit, is disclosed.

1 Drawing Sheet

Genus and species: *Dianthus caryophyllus*.
Variety denomination: 'KLEDP19263'.

BACKGROUND OF THE NEW PLANT

The present invention comprises a new and distinct variety of *Dianthus*, botanically known as *Dianthus caryophyllus*, and hereinafter referred to by the variety name 'KLEDP19263'. 'KLEDP19263' originated from a whole plant mutation from the *Dianthus* parent 'DCP-2004-0089' (unpatented) in The Netherlands in spring 2014.

In September 2014, 'KLEDP19263' was first vegetatively propagated by vegetative stem cuttings. 'KLEDP19263' was found to reproduce true to type in successive generations of asexual propagation in Stuttgart, Germany via vegetative stem cuttings.

SUMMARY

The following are the most outstanding and distinguishing characteristics of 'KLEDP19263' when grown under normal horticultural practices in Latina, Italy and Stuttgart, Germany.

1. Pink double flowers with red eyes, composed in round, small sprays; and
2. An upright habit.

DESCRIPTION OF THE PHOTOGRAPH

This new *Dianthus* plant is illustrated by the accompanying photograph. The photograph shows the whole plant, including the flowers and foliage and buds. The colors shown are as true as can be reasonably obtained by conventional photographic procedures. The photo is of a 14-week-old plant of 'KLEDP19263'. The photo was taken in Stuttgart, Germany, indoors, in September 2016.

DESCRIPTION OF THE NEW VARIETY

The following detailed descriptions set forth the distinctive characteristics of 'KLEDP19263'. The data which define these characteristics were collected from asexual reproductions carried out in Latina, Italy. Data was collected on plants potted in week 38 of 2018. Color references are to The R.H.S. Colour Chart of The Royal Horticultural Society of London (R.H.S.), 5$^{th}$ edition (2007).

Classification:
- *Family*.—Caryophyllaceae.
- *Botanical*.—*Dianthus caryophyllus*.
- *Common*.—Pot carnation.
- *Designation*.—'KLEDP19263'.

Parentage:
- *Mutation parent*.—'DCP-2004-0089'.

Plant:
- *Propagation type*.—Vegetative stem cuttings.
- *Time to produce a rooted young plant*.—4 weeks.
- *Rooting description and habit*.—Fine, white (RHS 155A), and lanceolate shaped.
- *Plant form*.—Upright, potted plant.
- *Plant height*.—23.0 cm.
- *Plant diameter or spread*.—25.0 cm.

Lateral branches:
- *Length*.—22.0 cm.
- *Diameter*.—0.2 cm.
- *Number of internodes*.—4 to 5.
- *Shape in cross-section*.—Slightly angular.
- *Hollowness*.—Absent.
- *Internode length*.—2.7 cm.
- *Node length*.—0.6 cm.

*Node diameter.*—0.1 cm.
*Texture.*—Smooth.
*Color.*—RHS 137B (Green).
*Flower clustering on the lateral branch.*—In some lateral branches.

Foliage:
*Arrangement.*—Opposite.
*Length.*—6.0 cm.
*Width.*—0.8 cm.
*Shape.*—Lanceolate.
*Apex.*—Acute.
*Base.*—Obtuse.
*Margin.*—Entire.
*Cross-section of the leaf.*—Weakly concave.
*Curvature of the leaf.*—Absent or weakly recurved.
*Glaucosity of the leaf.*—Weak.
*Texture (both upper and lower surfaces).*—Smooth.
*Immature leaf color.*—Upper surface: RHS N137C (Green). Lower surface: RHS 137A (Green).
*Mature leaf color.*—Upper surface: RHS N137D (Green). Lower surface: RHS 137A (Green).
*Venation pattern.*—Parallel.
*Venation color (both upper and lower surfaces).*—RHS N137A (Green).

Flowers:
*Flower type and habit.*—Round, double, small sprays.
*Fragrance.*—Present, sweet.
*Natural flowering season.*—Spring to fall.
*Flower longevity on the plant.*—10 to 12 days.
*Position of the flowers compared to the foliage.*—Same level.
*Profile of both the upper and lower part in the lateral view.*—Flat convex.
*Flower diameter.*—3.5 cm.
*Buds.*—Length: 1.8 cm. Diameter: 0.8 cm. Shape: Elliptic. Color: RHS 143A (Green). Extrusion of the styles of the bud: Present.
*Corolla.*—Quantity of petals per flower/arrangement: 28 in several whorls. Corolla height: 1.0 cm. Petal length: 2.8 cm. Petal width: 1.3 cm. Petal shape: Spoon-shaped. Petal apex: Obtuse. Petal base: Acute. Petal margin: Crenate. Petal color, immature and mature: Upper surface: RHS 62D (Red-Purple) with RHS 42D (Red) centers. Lower surface: RHS N155B (White) and RHS 2D (Yellow). Petal macule: Absent.
*Calyx.*—Quantity of sepals per flower: Composed of 5 sepals. Calyx height: 1.9 cm. Calyx diameter (at the apex): 0.8 cm. Shape: Cylindrical. Longitudinal axis of the lobes of the calyx: Straight. Sepal texture (both upper and lower surfaces): Smooth. Sepal color: Upper surface: RHS 137B (Green). Lower surface: RHS 144B (Yellow-Green).

Peduncles:
*Length.*—2.1 cm.
*Diameter.*—0.1 cm.
*Strength.*—Medium-weak.
*Texture.*—Smooth.
*Color.*—RHS 137B (Green).

Reproductive organs:
*Stamens.*—Quantity per flower: 4. Filament length: 0.7 cm. Filament color: RHS 1D (Yellow). Anther length: 0.1 cm. Anther diameter: 0.1 cm. Anther color: RHS 162A (Greyed-Yellow). Pollen amount: Absent.
*Pistils.*—Quantity per flower: 1. Pistil length: 2.5 cm. Style length: 1.4 cm. Style color: RHS NN155B. Description of the shoulder of the style: Absent. Stigma shape: Filamentous. Stigma color: RHS 69D (Red-Purple). Ovary size: 1.0 cm. Ovary shape: Obovate. Ovary color: RHS 144D (Yellow-Green). Ovary surface texture: Smooth.

Fruit and seed set: Not observed.

Disease and pest/insect resistance: No disease and pest/insect resistance observed.

COMPARISON OF 'KLEDP19263' WITH PARENTAL LINE AND KNOWN VARIETY

'KLEDP19263' is distinguished from the mutation parent as described in Table 1.

TABLE 1

Comparison with Parental Line

| Characteristic | 'KLEDP19263' | Mutation Parent 'DCP-2004-0089' |
|---|---|---|
| Flower color | Pink with red eye | Dark-pink with purple eye |

'KLEDP19263' can be compared to the commercial *Dianthus* variety 'DCP-2004-0089' and the commercial *Dianthus* variety 'KLEDP16230' (U.S. Plant Pat. No. 30,244). Differences between the varieties are described in Table 2.

TABLE 2

Comparison with Similar Variety

| Characteristic | 'KLEDP19263' | 'DCP-2004-0089' | 'KLEDP16230' |
|---|---|---|---|
| Flower color | Pink with red eye | Dark-pink with purple eye | Pink |

We claim:

1. A new and distinct variety of *Dianthus* plant designated 'KLEDP19263' as illustrated and described herein.

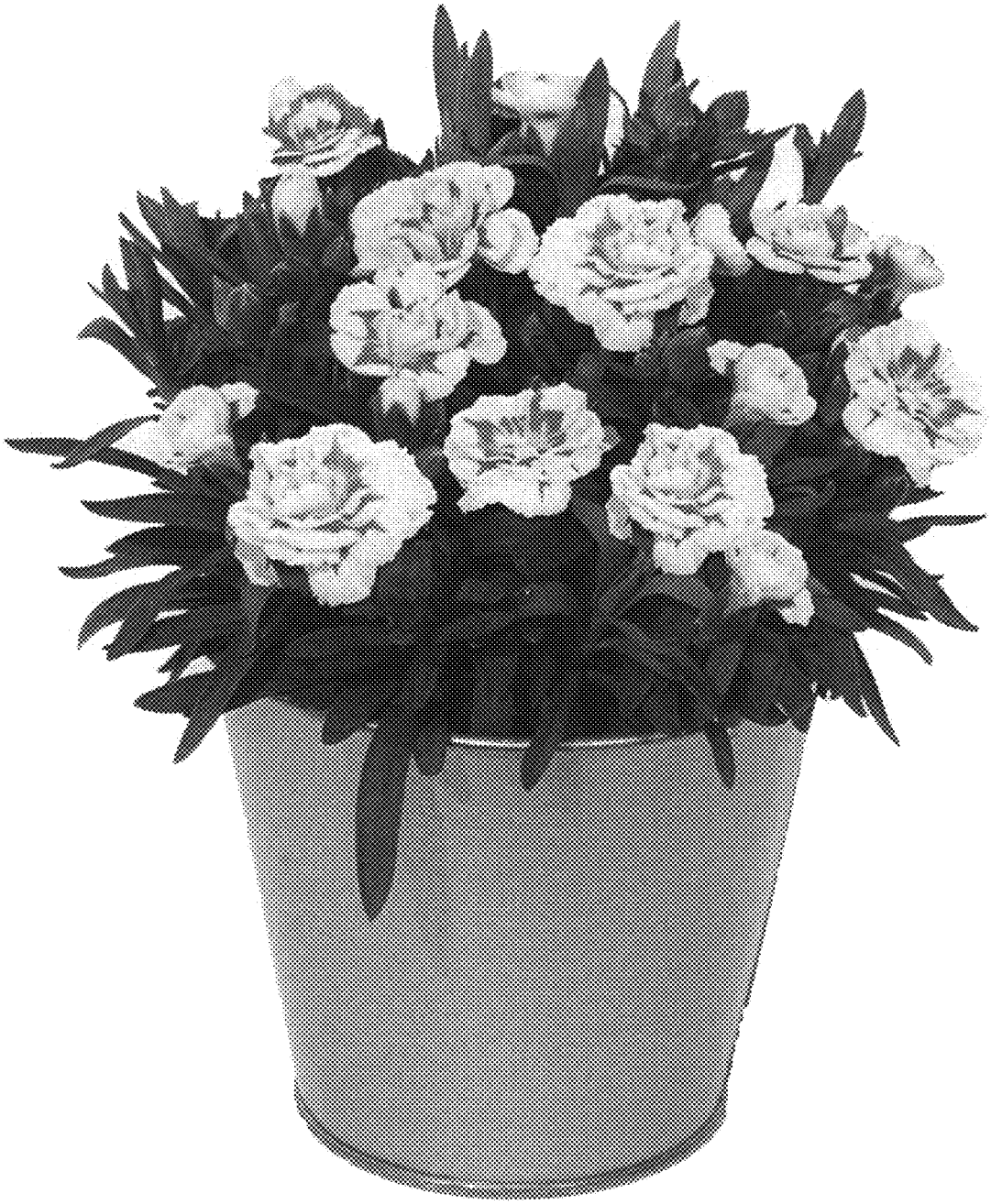

* * * * *